United States Patent
Dudnyk et al.

(10) Patent No.: US 11,517,644 B2
(45) Date of Patent: Dec. 6, 2022

(54) FOAM COMPOSITIONS, FOAM MATRICES AND METHODS

(71) Applicant: COVALON TECHNOLOGIES INC., Mississauga (CA)

(72) Inventors: Vyacheslav Dudnyk, Mississauga (CA); Mirzo Kanoatov, Toronto (CA); Valerio Ditizio, Toronto (CA)

(73) Assignee: COVALON TECHNOLOGIES INC., Mississauga (CA)

( * ) Notice: Subject to any disclaimer, the term of this patent is extended or adjusted under 35 U.S.C. 154(b) by 0 days.

(21) Appl. No.: 16/671,975

(22) Filed: Nov. 1, 2019

(65) Prior Publication Data

US 2020/0139002 A1  May 7, 2020

Related U.S. Application Data

(60) Provisional application No. 62/754,698, filed on Nov. 2, 2018.

(51) Int. Cl.

| | | |
|---|---|---|
| *A61L 15/42* | (2006.01) | |
| *C08J 9/12* | (2006.01) | |
| *A61L 15/32* | (2006.01) | |
| *A61L 15/64* | (2006.01) | |
| *A61L 15/44* | (2006.01) | |
| *A61L 15/22* | (2006.01) | |

(52) U.S. Cl.
CPC ........... *A61L 15/425* (2013.01); *A61L 15/225* (2013.01); *A61L 15/32* (2013.01); *A61L 15/44* (2013.01); *A61L 15/64* (2013.01); *C08J 9/125* (2013.01); *A61L 2300/404* (2013.01); *A61L 2300/418* (2013.01); *A61L 2400/04* (2013.01); *C08J 2203/10* (2013.01); *C08J 2389/04* (2013.01); *C08J 2405/04* (2013.01)

(58) Field of Classification Search
CPC ........ A61L 15/225; A61L 15/32; A61L 15/44; A61L 15/64; C08J 9/125
See application file for complete search history.

(56) References Cited

U.S. PATENT DOCUMENTS

| | | | |
|---|---|---|---|
| 2,465,357 A | | 3/1949 | Correll |
| 4,292,972 A | | 10/1981 | Pawelchak et al. |
| 4,530,905 A | * | 7/1985 | Freedman ........... C08G 18/6446 435/177 |
| 4,703,108 A | * | 10/1987 | Silver .................... A61L 27/24 530/356 |
| 5,324,775 A | * | 6/1994 | Rhee ..................... A61K 47/61 525/54.2 |
| 5,840,777 A | * | 11/1998 | Eagles .................... A61L 15/28 521/82 |
| 5,851,461 A | * | 12/1998 | Bakis .................... A61L 15/28 264/50 |
| 8,703,170 B2 | * | 4/2014 | Hedrich ................ A61L 15/425 424/426 |
| 8,961,544 B2 | * | 2/2015 | Komlos ................. A61L 15/38 606/151 |
| 9,375,505 B2 | * | 6/2016 | Hedrich .................. A61L 15/18 |
| 2002/0164322 A1 | | 11/2002 | Schaufler |
| 2006/0068013 A1 | * | 3/2006 | DiTizio ................. A61L 15/325 424/484 |
| 2007/0254016 A1 | * | 11/2007 | Andersen ............... A61K 9/122 424/443 |
| 2011/0045034 A1 | | 2/2011 | Nur et al. |
| 2013/0344131 A1 | * | 12/2013 | Lo .......................... A61L 15/28 424/447 |
| 2015/0196683 A1 | * | 7/2015 | Iram ........................ A61P 7/04 424/94.5 |
| 2016/0074553 A1 | * | 3/2016 | Reyes Ortega ...... A61K 9/7092 424/444 |
| 2018/0064580 A1 | * | 3/2018 | Hussain .................. A61L 27/20 |
| 2019/0160198 A1 | * | 5/2019 | Levinson ............... A61L 15/32 |

FOREIGN PATENT DOCUMENTS

| | | |
|---|---|---|
| KR | 101613403 B1 | 4/2016 |
| WO | WO 2007/103208 A2 | 9/2007 |
| WO | WO 2008/121279 A1 | 10/2008 |

OTHER PUBLICATIONS

Awad et al., "Chondrogenic differentiation of adipose-derived adult stem cells in agarose, alginate, and gelatin scaffolds," Biomaterials, 25(16):3211-3222, (2004).

Fang et al., "Adhesion contact dynamics of fibroblasts on biomacromolecular surfaces," Macromol Biosci., 5(10):1022-1031, (2005).

Postlethwaite et al., "Chemotactic attraction of human fibroblasts to type I, II, and III collagens and collagen-derived peptides," Proc Natl Acad Sci U S A., 75(2):871-875, (1978).

Postlethwaite et al., "Induction of fibroblast chemotaxis by fibronectin. Localization of the chemotactic region to a 140,000-molecular weight non-gelatin-binding fragment," J Exp Med.,53(2):494-499, (1981).

Yang et al., "Biological Behaviors of Keratinocytes Cultured on Chitosan-Gelatin Membrane," Key Engineering Materials, 288-289:401-404, (2005).

Zhu et al., "Endothelium regeneration on luminal surface of polyurethane vascular scaffold modified with diamine and covalently grafted with gelatin," Biomaterials, 25(3):423-430, (2004).

WIPO Application No. PCT/CA2019/051553, PCT International Search Report and Written Opinion of the International Searching Authority dated Jan. 3, 2020.

(Continued)

*Primary Examiner* — Robert A Wax
*Assistant Examiner* — Olga V. Tcherkasskaya
(74) *Attorney, Agent, or Firm* — Alston & Bird LLP

(57) ABSTRACT

Disclosed herein are matrices, compositions and methods of making matrices. The matrix comprises a biomolecule and the matrix is a dried, cross-linked foam. The matrix is not lyophilized. The method comprises foaming the composition, crosslinking the composition and drying the composition. Matrices disclosed herein are useful as wound dressings and treating wounds.

18 Claims, No Drawings

(56) References Cited

OTHER PUBLICATIONS

Meyer, Michael et al., "Soft Collagen—Gelatin Sponges by Convectin Drying," Brazilian Archives of Biology and Technology, 58(1):109-117, (Jan.-Feb. 2015).
European Application No. 19879872.0, Extended EP Search Report dated Jun. 27, 2022.

\* cited by examiner

FOAM COMPOSITIONS, FOAM MATRICES AND METHODS

CROSS-REFERENCE TO RELATED APPLICATIONS

This application claims the benefit of U.S. Provisional Application No. 62/754,698, entitled "FOAM COMPOSITIONS, FOAM MATRICES AND METHODS", and filed Nov. 2, 2018, the entire contents of which are hereby incorporated by reference.

FIELD

The present invention relates to matrices. More specifically, the present invention is, in aspects, concerned with foamed matrices, and related compositions, methods of making and using same.

BACKGROUND

Gelatin- and collagen-based materials have hemostatic ability and as such, gelatin and collagen sponges have been used as effective tools to control wound bleeds. Typically, gelatin-based materials are stabilized in some way so that they are durable when applied to human skin or tissue. Methods of stabilizing gelatin-based materials include chemical treatments, heat treatments and crosslinking methods.

U.S. Pat. No. 2,465,357 describes a liquid-permeable, water-insoluble, gelatin sponge having the general physical characteristics of a sponge but being absorbable by animal bodies.

U.S. Pat. No. 4,703,108 describes a process for preparing biodegradable collagen-based matrices in sponge or sheet form wherein a collagen-based material is freeze dried to form a collagen-based sponge which is contacted with a cross-linking agent to form an intermediate collagen-based matrix which is subsequently subjected to conditions of severe dehydration to form the collagen-based matrix in sponge or sheet form.

U.S. Pat. No. 8,361,501 describes a substantially non-adhesive elastic gelatin matrix. The matrix is both non-adhesive to wounds, tissues and organs and is also elastic such that it is flexible. The matrix is a lyophilized mixture of protein(s), polymer(s), cross-linking agent(s) and optional plasticizer(s). Methods for making the non-adhesive elastic gelatin matrix are also described.

There is a need for alternative matrices and compositions to overcome or mitigate at least some of the deficiencies of the prior art, or to provide a useful alternative.

SUMMARY

In accordance with an aspect, there is provided a matrix comprising: a biomolecule; wherein the matrix is a dried, cross-linked foam.

In aspects, the matrix is non-lyophilized.

In aspects, the biomolecule is selected from the group consisting of gelatin, collagen, elastin, and combinations thereof.

In aspects, the biomolecule is present at about 40% to about 80% (w/w).

In aspects, the matrix described herein further comprises at least two layers.

In aspects, the at least two layers are substantially identical with respect to the biomolecule content and/or an amount of crosslinking relative to an adjacent foam layer.

In aspects, the at least two layers are different with respect to the biomolecule content and/or an amount of crosslinking relative to an adjacent foam layer.

In aspects, the matrix is free of a hardened "skin" and/or a compacted "skin" on a surface of the matrix.

In aspects, the matrix described herein further comprises at least one biocompatible polymer.

In aspects, the biocompatible polymer is selected from the group consisting of polyethylene glycol, poly-L-lysine, alginate, chitosan, hyaluronic acid, chondroitin sulfate, pectin, cellulose, carboxymethylcellulose and mixtures thereof.

In aspects, the biocompatible polymer is present in about 0.4% to about 25% (w/w).

In aspects, the matrix has a pore size ranging from about 100 μm to about 750 μm.

In aspects, the matrix has an absorption capacity of about 20 times to about 50 times a dry weight of the dried, crosslinked foam matrix.

In aspects, the matrix has a thickness of at least 1 mm.

In aspects, the matrix further comprises an active agent.

In aspects, the active agent is selected from the group consisting of an antimicrobial agent, an analgesic agent, an anti-adhesion compound, an anti-tumor drug, an anti-proliferative drug, a chelator and combinations thereof.

In aspects, the antimicrobial agent is selected from the group consisting of chlorhexidine, octenidine, benzalkonium chloride, benzethonium chloride, polyhexamethylene biguanide, copper, zinc, silver, chlorine, an active chlorine compound, fluoroquinolones, b-lactams, macrolides, aminoglycosides, tetracyclines, and combinations thereof.

In aspects, the antimicrobial agent comprises silver ions.

In aspects, the silver ions are derived from a silver salt selected from the group consisting of silver phosphate, silver sulfate, silver citrate, silver lactate, silver acetate, silver benzoate, silver chloride, silver carbonate, silver iodide, silver iodate, silver nitrate, silver laurate, silver sulfadiazine, silver palmitate, and mixtures thereof.

In aspects, the active agent is present at about 0.1% to 30% (w/w).

In aspects, the active agent is present in and/or on one of the at least two layers.

In aspects, the active agent is present in and/or on both of the at least two layers.

In aspects, the active agent, the biomolecule and/or the biocompatible polymer is evenly distributed through and/or on both of the at least two layers.

In aspects, the active agent, the biomolecule and/or the biocompatible polymer is non-uniformly distributed through and/or on both of the at least two layers.

In aspects, the matrix is cross-linked using a crosslinking agent.

In aspects, the crosslinking agent is selected from the group consisting of 1-ethyl-3-(3-dimethylaminopropyl)carbodiimide (EDC), N-hydroxysuccinimide (NHS) and mixtures thereof.

In aspects, the crosslinking agent is present in about 0.5% to about 5% (w/w).

In aspects, the matrix is fabricated as a covering.

In aspects, the covering is selected from the group consisting of a wound barrier, a wound dressing, a hemostatic dressing, a vascular wrap, a sponge, a gauze, a bandage, a film, a sheet, a tube and combinations thereof.

In aspects, the matrix is for use as a wound barrier, a wound dressing, a hemostatic dressing, a vascular wrap, a sponge, a gauze, a bandage, a film, a sheet, a tube and combinations thereof.

In aspects, the matrix is for use in delivery of an active agent to a surface.

In aspects, the matrix is for use in treating in a wound.

In accordance with another aspect, there is provided a composition for forming a foamed, cross-linked and non-lyophilized matrix, the composition comprising: a biomolecule, wherein the composition is foamable and the biomolecule is crosslinkable.

In aspects, the composition described herein further comprises a pharmaceutically acceptable excipient.

In aspects, the pharmaceutically acceptable excipient is selected from the group consisting of a diluent, a disintegrant, a glidant, a binder, a lubricant, an antioxidant, a preservative, a coloring agent, a flavoring agent, an emulsifying agent, a suspending agent, a pharmaceutical solvent and combinations thereof.

In aspects, the biomolecule is selected from the group consisting of gelatin, collagen, elastin, and combinations thereof.

In aspects, the biomolecule is present at about 40% to about 80% (w/w).

In aspects, the composition described herein further comprises an active agent.

In aspects, the active agent is selected from the group consisting of an antimicrobial agent, an analgesic agent, an anti-adhesion compound, an anti-tumor drug, an anti-proliferative drug, a chelator and combinations thereof.

In aspects, the antimicrobial agent is selected from the group consisting of chlorhexidine, octenidine, benzalkonium chloride, benzethonium chloride, polyhexamethylene biguanide, copper, zinc, silver, chlorine, an active chlorine compound, fluoroquinolones, b-lactams, macrolides, aminoglycosides, tetracyclines, and combinations thereof.

In aspects, the antimicrobial agent comprises silver ions.

In aspects, the silver ions are derived from a silver salt selected from the group consisting of silver phosphate, silver sulfate, silver citrate, silver lactate, silver acetate, silver benzoate, silver chloride, silver carbonate, silver iodide, silver iodate, silver nitrate, silver laurate, silver sulfadiazine, silver palmitate, and mixtures thereof.

In aspects, the active agent is present at about 0.1% to 30% (w/w).

In aspects, the composition further comprises a crosslinking agent.

In aspects, the crosslinking agent is selected from the group consisting of 1-ethyl-3-(3-dimethylaminopropyl)carbodiimide (EDC), N-hydroxysuccinimide (NHS) and mixtures thereof.

In aspects, the crosslinking agent is present in about 0.5% to about 5% (w/w).

In aspects, the composition further comprises at least one biocompatible polymer.

In aspects, the biocompatible polymer is selected from the group consisting of polyethylene glycol, poly-L-lysine, alginate, chitosan, hyaluronic acid, chondroitin sulfate, pectin, cellulose, carboxymethyl cellulose and mixtures thereof.

In aspects, the biocompatible polymer is present in about 0.4% to about 25% (w/w).

In accordance with another aspect, there is provided a use of the matrix described herein for reducing microorganism growth on a surface.

In aspects, the microorganism is selected from the group consisting of *Candida albicans, Escherichia coli*, and antibiotic-resistant *Enterococcus*.

In aspects, the surface is skin or a medical device.

In accordance with another aspect, there is provided a use of the matrix described herein as a wound dressing, a bandage, or a sponge.

In accordance with yet another aspect, there is provided a use of the composition described herein for forming a foamed, crosslinked, non-lyophilized matrix for reducing microorganism growth on a surface.

In aspects, the microorganism is selected from the group consisting of *Candida albicans, Escherichia coli*, and antibiotic-resistant *Enterococcus*.

In aspects, the surface is skin or a medical device.

In accordance with yet another aspect, there is provided a method of treating a wound comprising applying the matrix described herein to the wound.

In accordance with a further aspect, there is provided a use of the matrix described herein to treat a wound.

In accordance with still a further aspect, there is provided a method for making a matrix comprising: foaming a composition comprising a biomolecule; crosslinking the composition; and drying the composition.

In aspects, the composition described herein further comprises a pharmaceutically acceptable excipient.

In aspects, the pharmaceutically acceptable excipient is selected from the group consisting of a diluent, a disintegrant, a glidant, a binder, a lubricant, an antioxidant, a preservative, a coloring agent, a flavoring agent, an emulsifying agent, a suspending agent, a pharmaceutical solvent and combinations thereof.

In aspects, the biomolecule is selected from the group consisting of gelatin, elastin, collagen, and combinations thereof.

In aspects, the crosslinking is carried out after foaming.

In aspects, the crosslinking is carried out while foaming.

In aspects, the crosslinking comprises adding a crosslinking agent.

In aspects, the crosslinking agent is selected from the group consisting of 1-ethyl-3-(3-dimethylaminopropyl)carbodiimide (EDC), N-hydroxysuccinimide (NHS) and mixtures thereof.

In aspects, the adding is done in a dropwise manner.

In aspects, the composition described herein further comprises at least one biocompatible polymer.

In aspects, the at least one biocompatible polymer is selected from the group consisting of polyethylene glycol, poly-L-lysine, alginate, chitosan, hyaluronic acid, chondroitin sulfate, pectin, cellulose, carboxymethylcellulose and mixtures thereof.

In aspects, the composition described herein further comprises an active agent.

In aspects, the active agent does not substantially affect the foaming.

In aspects, the method described herein further comprises layering an active agent onto the matrix.

In aspects, the active agent is in a powdered or concentrated liquid form.

In aspects, the active agent is selected from the group consisting of an antimicrobial agent, an analgesic agent, an anti-adhesion compound, an anti-tumor drug, an anti-proliferative drug, a chelator and combinations thereof.

In aspects, the antimicrobial agent is selected from the group consisting of chlorhexidine, octenidine, benzalkonium chloride, benzethonium chloride, an active chlorine compound, polyhexamethylene biguanide, copper, zinc, silver, chlorine, fluoroquinolones, b-lactams, macrolides, aminoglycosides, tetracyclines, and combinations thereof.

In aspects, the antimicrobial agent comprises silver ions.

In aspects, the silver ions are derived from a silver salt selected from the group consisting of silver phosphate, silver sulfate, silver citrate, silver lactate, silver acetate, silver benzoate, silver chloride, silver carbonate, silver iodide, silver iodate, silver nitrate, silver laurate, silver sulfadiazine, silver palmitate, and mixtures thereof.

In aspects, the method described herein further comprises heating the composition.

In aspects, the heating is carried out prior to foaming.

In aspects, the heating takes place at about 50° C.

In aspects, the method described herein further comprises cooling the composition.

In aspects, the cooling is carried out prior to foaming.

In aspects, the cooling takes place at about 25° C. to about 28° C.

In aspects, the cooling takes place at about 26° C.

In aspects, the cooling is carried out with continuous stirring of the composition.

In aspects, the method described herein further comprises transferring the matrix to a tray or mold.

In aspects, the transferring is carried out prior to drying.

In aspects, the tray or mold is lined with a hydrophobic film.

In aspects, the transferring step comprises spreading the matrix in the tray or mold.

In aspects, the drying step comprises air-drying.

In aspects, the air-drying is carried out at ambient pressure and temperature.

In aspects, the air-drying is carried out at about 40° C.

In aspects, the drying ensures efficient air circulation around the matrix.

In aspects, the drying is up to 48 hours.

In aspects, the drying is not freeze drying.

In aspects, the matrix is free of a hardened skin and/or a compacted skin on a surface of the matrix.

In accordance with still yet another aspect, there is provided a wound dressing comprising the matrix described herein.

In accordance with still yet another aspect, there is provided a matrix made by the method described herein.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from said detailed description.

DETAILED DESCRIPTION

Described herein, in aspects, are matrices, compositions for forming the matrices and methods of forming the matrices from the compositions. In aspects, the methods described herein utilize a foaming and air-drying technique which is readily employable and produces matrices as described herein without any undesirable surface layers that would need to be removed with further processing techniques as described further below.

Definitions

As used herein, a "foamed matrix" or "foam" is formed from a mass of small bubbles formed on or in liquid, typically by agitation. The process of "foaming" involves producing a mass of small bubbles, similar to the formation of a froth. For example, a foam may be produced by whipping a composition described herein much like one would whip cream. Foams may also be produced by bubbling air through a composition described herein.

As used herein, a "bandage" means a piece of cloth or other material used to bind or wrap a diseased or injured part of the body. Bandages are either placed directly against the wound or used to bind a wound dressing to the wound.

As used herein, a "wound dressing", "hemostatic dressing", "vascular wrap", "sponge" or "gauze" means a piece of cloth or material that is placed directly against the wound and serves the purpose of protecting the wound; stopping or reducing bleeding; promoting healing; and/or providing, retaining, or removing moisture, and is optionally held in place using a bandage.

As used herein, "active chlorine compound" refers to a compound containing active chlorine, (chlorine which has oxidizing properties similar to those of elemental chlorine). Such compounds usually contain a chlorine atom attached to an oxygen atom or to a nitrogen atom. Compounds of this type are useful in industrial textile bleaching, as germicides, as constituents of bleaching, sanitizing and detergent compositions, and for other purposes. Active chlorine compounds include but are not limited to, sodium and potassium dichloroisocyanurate, di- and trichlorocyanuric acid, trichloro melamine, Chloramine T (sodium N-chloro-p-toluene-sulfonamide), dichlorodimethyl hydantoin, sodium, calcium and lithium hypochlorites, and the like.

As used herein, the term "anti-tumor drug" refers to a chemotherapeutic agent that partially, substantially, or completely eliminates a tumor. Exemplary anti-tumor drugs include, but are not limited to, alkylating agents such as Nitrogen mustards, nitromin, chlorambucil, cyclophosphamide, melphalan, uracil mustard, mannomustine, dopan, BCNU, triethylenemelamine, thio-tetraethylenepenramine (TEPA), Aza-TEPA, threnimone, inprocuon, busulfan, dimethylmilelane, piposulfan, ethoglucide, epoxypropidine, epoxypiperazine, hexamethylmelamine, dibromomannitol, pipobroman, 1-(2-chloroethyl)-3-cyclohexyl-1-nitrosourea (CCNU), methyl-CCNU, chlorozotocin, 1-(2-chloroethyl)-3-(β-D-glucopyranosyl)-1- nitrosourea (GANU), 1-(2-chloroethyl)-3-(methyl α-glucopyranos-6-yl)-1-nitrosourea (MCNU), 3[(4-amino-2-methyl-5-pyrimidinyl)methyl]-I-(2-ehloro-ethyl)-1-nitrosoureahydrochloride (ACNU), TA-077 and fosamid; antimetabolites such as folic acid, aminopterin, methotrexate, guanine, 8-azaguanine, 6-mercaptopurine, azathioprine, uracil, 5-fluorouracil, cytarabine, azaserine, diazamycin, behenoyl Ara-C (BHAC), SM108, cispuracham, cytosine arabinoside, tegaful, 1-hexylcarbamoyl-5-fluorouracil (HCFU), 5'-deoxy-5-fluorouridine (5'DFUR), TK-117 and cyclotidine; antibiotics such as actinomycin D, cyclomycin, mitomycin C, daunomycin, bleomycin, cromomycin, carzinophyllin, macrocinomycin, neothramycin, thalisomycin, sporamycin, saframycin, ansamytocin, 6-diazo-5-oxo -L-norleucine (DON), macromomycin, nogaromycin, 7-o-methylnogallol-4'-epiadriamycin, streptozotocin, 4-demethoxydaunorubicin and mitozanthron; synthetic agents such as 5-hydroxypicolinaldehyde thiosemicarbazone (5-HP) and 1-formylisoquinoline thiosemicarbazones (IQ-1); plant components such as thiotepa, cyclophosphamide, doxorubicin, daunorubicin and neocarzinostain; and Hg-hematoporphyrine, Co-protoporphyrine, stillbestrol, hydroxyurea, procarbazine, methylglyoxalbis-guanylhydrazone, L-asparaginase and tumor necrosis factor (TNF).

As used herein, the term "anti-proliferative drug" refers to anti-metabolites that act by inhibiting crucial metabolic processes and are commonly used in the treatment of diseases involving abnormal cell proliferation, such as tumors. The anti-tumor drugs described above are, in some cases, also consider anti-proliferative drugs.

As used herein, the term "analgesic agent" refers to a substance that has a pain relieving effect. Analgesic agents include, but are not limited to, non-opioid analgesic agent such as acetylsalicylic acid acetaminophen, paracetamol, ibuprofen, ketoprofen, ketoconazole, indomethacin, diflunisol, naproxen, ketorolac, dichlophenac, tolmetin, sulindac, phenacetin, piroxicam, mefamanic acid, dextromethorphan, other non-steroidal anti-inflammatory drugs including salicylates, pharmaceutically acceptable salts thereof and mixtures thereof; or opioid analgesic agent such as codeine, morphine, hydromorphine, levophanol, meperidine, meptazinol, propoxyphene, propiram, buprenorphine, pentazocine, nalbuphine, butorphanol, tramadol, hydrocodone, oxycodone, methadone, pharmaceutically acceptable salts thereof and mixtures thereof. Such pharmaceutically acceptable salts include, but are not limited to hydrochloride, hydrobromide, phosphate, sulfate, acetate, succinate, ascorbate, tartrate, gluconate, benzoate, malate, fumarate, and the like.

As used herein, the term "anti-adhesion compound" refers to a compound (or polymer in the form of a film or a liquid) that can be used to prevent postoperative adhesion (e.g., scar) formation. Exemplary anti-adhesion compounds include, but are not limited to, polylactic acid, polyethylene glycol berberine liquid (PEG), sodium hyaluronate, and chitosan.

As used herein, the term "chelator" refers to a substance that has the ability to able to capture or remove free ions or facilitate its removal from a target tissue, thus impairing its catalytic activity and protecting the skin. An exemplary chelators include, but are not limited to, desferrioxamine, diethylenetriaminepentaacetic acid, N, N'-bis (o-hydroxybenzyl) ethylenediamine-N, N'-diacetic acid, 1,2-dimethyl-3-hydroxypyrid-4-one and 1,2-dimethyl-3-hydroxyl-3-hydroxypyridine-4-one.

As used herein, the term "antimicrobial agent" refers to any agent that is capable of partially, substantially or completely eliminating a microbe. Examples of anti-microbial agents include, antibacterial agents, antiviral agents, antifungal agents and innate immune peptide or proteins as described herein.

As used herein, the term "pharmaceutically acceptable" means that the compound or combination of compounds is compatible with the remaining ingredients of a formulation or composition for pharmaceutical use, and that it is generally safe for administering to humans according to established governmental standards, including those promulgated by the United States Food and Drug Administration.

As used herein, the term "excipient" means a non-active ingredient that can be added to the compositions or matrices described herein. Examples of excipients would be understood by persons skilled in the art, and some examples are provided in the description below.

As used herein, the term "air-drying" encompasses any method of drying that is carried out above freezing temperature. For example, the matrix described herein is dried after the moist foam is produced, at ambient temperature and pressure. Drying under this method can or cannot be done under a vacuum to remove trace solvents (e.g., if the matrix is dried at room temperature then the sample may be dried in a vacuum desiccator or if the matrix is dried above room temperature then the matrix may be dried in a vacuum drying oven).

The term "lyophilization" encompasses removing water droplets from a matrix (leaving holes in the matrix) after it is frozen and placed under a vacuum, thereby allowing ice to change directly from solid to vapor without passing through a liquid phase under low temperature and pressure. In this way, the product (e.g., matrix) is never exposed to temperatures above freezing during the drying process. Lyophilization and freeze-drying are used interchangeably herein.

Matrices made by these two different processes (air-drying and lyophilization) are not the necessarily the same products as they tend to have different structural properties. For example, air-dried products tend to be more compact and durable (e.g., resistant to crumbling), whereas products that are freeze-dried tend to be less compact and more fragile (e.g., crush easily). Despite this, the air-dried matrices described herein perform at least equally well as freeze-dried products, as exemplified herein. Accordingly, the methods described herein can produce durable foamed matrices (e.g., sponges) which are suitable as a compact wound dressing.

In understanding the scope of the present application, the articles "a", "an", "the", and "said" are intended to mean that there are one or more of the elements. Additionally, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

It will be understood that any aspects described as "comprising" certain components may also "consist of" or "consist essentially of," (or vice versa) wherein "consisting of" has a closed-ended or restrictive meaning and "consisting essentially of" means including the components specified but excluding other components except for materials present as impurities, unavoidable materials present as a result of processes used to provide the components, and components added for a purpose other than achieving the technical effects described herein. For example, a composition defined using the phrase "consisting essentially of" encompasses any known pharmaceutically acceptable additive, excipient, diluent, carrier, and the like. Typically, a composition consisting essentially of a set of components will comprise less than 5% by weight, typically less than 3% by weight, more typically less than 1% by weight of non-specified components.

It will be understood that any component defined herein as being included may be explicitly excluded by way of proviso or negative limitation, such as any specific compounds or method steps, whether implicitly or explicitly defined herein. For example, in aspects, methods involving lyophilization are explicitly excluded from the methods described herein. Likewise, in aspects, the matrices described herein are not lyophilized.

In addition, all ranges given herein include the end of the ranges and also any intermediate range points, whether explicitly stated or not.

Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Matrices

Described herein is a matrix comprising a biomolecule, wherein the matrix is a dried, crosslinked foam. Advantageously, the matrix described herein does not require lyophilization. Rather, it can be simply air-dried under, for example, ambient conditions.

The biomolecule may be a dry component that is biocompatible and is crosslinkable to form a three-dimensional matrix. The biomolecule is typically biodegradable, and, when formed into a matrix, is capable of absorbing fluid. In aspects, the absorption of fluid is many times a weight of the matrix described herein. In typical aspects, the biomolecule is selected from gelatin, collagen, elastin, and combinations thereof. Typically, the biomolecule is gelatin.

The matrices described herein may be formed as a single layer or as multiple layers. If the matrix comprises multiple layers, the layers may be joined together to form an integral composite.

In aspects, the matrices comprise at least two layers. In aspects, the at least two layers can be substantially identical with respect to the biomolecule content and/or the amount of crosslinking relative to an adjacent foam layer. For example, if the matrix has two layers, both of the layers would have similar amounts (e.g., concentration) of biomolecule or both layers would have a similar extent of crosslinking.

In aspects, the biomolecule content and/or the amount of crosslinking relative to the adjacent foam layer are different. For example, if the matrix has two layers, one layer may have a high proportion (e.g., concentration) of biomolecule than the second layer. In a similar way, one of the layers may have an increased extent of crosslinking when compared to the other layer.

It would be understood that the amount of biomolecule and/or the extent of crosslinking of the layer(s) of the matrix can be varied by, for example, adding increased amounts of biomolecules and/or crosslinking agents when forming the layer(s) of the matrix. In this way, each layer of, or a single layer of the matrix described herein may have different physiochemical properties. For example, differences in crosslinking extent or concentrations of the biomolecule within the layer(s) of the matrix may influence the absorptive properties of the matrix described herein. For example, by increasing the amount of biomolecule in a layer(s) of the matrix, especially a layer closest to the skin, the absorptive capacity of the matrix may be increased (e.g., the amount of fluid that can be retained by the matrix when applied to the skin). Additionally or alternatively, the extent of crosslinking of the biomolecule described herein may influence the tensile strength or elongation properties of the matrix, thereby impacting its effectiveness as a wound dressing. Accordingly, these factors can be taken into account when producing the matrices by the methods described herein.

When conventional compositions are lyophilized to produce a matrix, it is typically a liquid composition poured into a mold, which is then lyophilized. This liquid can have a tendency to form a hardened or compacted skin on the surface when dried. Because the compositions and matrices described herein are foamed and are not in liquid form, they do not tend to form similar skins as they dry. Thus, in aspects, the matrices described herein are free of a hardened "skin" and/or a compacted "skin" on a surface of the matrix. This "skin" is similar to a film that can form on the surface of the matrix. Typically, the surface is a surface that makes contact with a drying apparatus (i.e., a drying-container contacting side) during the air-drying process described herein. As the matrices produced by the methods described herein are free of this "skin", the matrices described herein do not require further processing to remove the "skin", as is typical with other matrices.

In aspects, the matrices described herein further comprise at least one biocompatible polymer. Typically, the biocompatible polymer is selected from, but is not limited to, polyethylene glycol, poly-L-lysine, alginate, chitosan, hyaluronic acid, chondroitin sulfate, pectin, cellulose, carboxymethylcellulose and mixtures thereof. Typically, the biocompatible polymer is alginate or carboxymethylcellulose.

The matrices described herein are porous. In aspects, the matrices described herein have pore sizes ranging from about 100 μm to about 750 μm. The pore sizes can be 90 μm, 95 μm, 100 μm, 110 μm, 150 μm, 175 μm, 200 μm, 250 μm, 300 μm, 400 μm, 450 μm, 500 μm, 600 μm, 650 μm, 700 μm, 750 μm or 800 μm (or any value therebetween).

Typically, the matrices described herein are absorbent. In aspects, the matrices described herein have an absorption capacity of about 20 times to about 50 times a dry weight of the matrix formed by the methods described herein. For example, the absorption capacity can be 15, 20, 25, 30, 35, 40, 45, 50, or 55 times the dry weight of the matrix formed by the methods described herein. This absorptive capacity contributes to the ability of the matrices described herein to function as, for example, a wound dressing and/or hemostatic dressing.

In typical aspects, the matrices described herein have a thickness of at least 1 mm. It will be understood that the thickness of the matrix can be varied by either, for example, adjusting the amount of foam poured into a mold, or by increasing the numbers of layers. Modifying the thickness of the matrix may be appropriate to, for example, increase the volume of the matrix to which fluid (e.g., blood or wound exudate) may fill or be absorbed by the matrix.

The matrices described herein are dried by any known method. Typically, the method of drying excludes lyophilization. In typical aspects, the matrices are air-dried, under, for example, ambient conditions. For example, the matrix can be dried at room temperature and pressure. This is a simple and inexpensive method to dry the matrices and no specialized equipment is required. In aspects, ventilators are used to ensure efficient air circulation around the matrix (e.g., drying around the matrix does not leave wet spots). In this way, the foam matrix that is produced by the methods described herein is no longer a moist foam and is able to absorb fluids when placed in contact therewith. As described above, the air-drying technique used to make the matrices described herein advantageously simplifies the method described herein for producing the matrix but also eliminates the production of a hardened or compacted skin on the surface of the matrix.

In aspects, the matrices described herein further comprise an active agent. The active agent includes, but is not limited to, an antimicrobial agent, an analgesic agent, an anti-adhesion compound, an anti-tumor drug, an anti-proliferative drug, a chelator and combinations thereof.

The active agent, in aspects, is an antimicrobial agent, including one or more antibacterial agents, and/or one or more antifungal agents, and/or one or more antiviral agents, and/or one or more antiseptic agents, and/or combinations thereof.

In typical aspects, the antimicrobial agent is an antibacterial agent. While any antibacterial agent as described herein may be used in the compositions described herein, some non-limiting exemplary antibacterial agent include those classified as aminoglycosides, beta lactams, quinolones or fluoroquinolones, macrolides, sulfonamides, sulfamethaxozoles, tetracyclines, streptogramins, oxazolidinones (such as linezolid), clindamycins, lincomycins, rifamycins, glycopeptides, polymxins, lipo-peptide antibiotics, metal salts, as well as pharmacologically acceptable sodium salts, pharmacologically acceptable calcium salts, pharmacologically acceptable potassium salts, lipid formulations, derivatives and/or analogs of the above.

In other aspects, the antimicrobial agent includes an antifungal agent. Some exemplary classes of antifungal agents include imidazoles or triazoles such as clotrimazole, miconazole, ketoconazole, econazole, butoconazole, omoconazole, oxiconazole, terconazole, itraconazole, fluconazole, voriconazole (UK 109,496), posaconazole, ravuconazole or flutrimazole; the polyene antifungals such as amphotericin B, liposomal amphoterecin B, natamycin, nystatin and nystatin lipid formulations; the cell wall active cyclic lipopeptide antifungals, including the echinocandins such as caspofungin, micafungin, anidulfungin, cilofungin; LY121019; LY303366; the allylamine group of antifungals such as terbinafine. Yet other non-limiting examples of antifungal agents include naftifine, tolnaftate, mediocidin, candicidin, trichomycin, hamycin, aurefungin, ascosin, ayfattin, azacolutin, trichomycin, levorin, heptamycin, candimycin, griseofulvin, BF-796, MTCH 24, BTG-137586, pradimicins (MNS 18184), benanomicin; ambisome; nikkomycin Z; flucytosine, or perimycin.

In still other aspects, the antimicrobial includes an antiviral agent. Non-limiting examples of antiviral agents include cidofovir, amantadine, rimantadine, acyclovir, gancyclovir, pencyclovir, famciclovir, foscarnet, ribavirin, or valcyclovir.

In some aspects the antimicrobial agent is an innate immune peptide or proteins. Some exemplary classes of innate peptides or proteins are transferrins, lactoferrins, defensins, phospholipases, lysozyme, cathelicidins, serprocidins, bacteriocidal permeability increasing proteins, amphipathic alpha helical peptides, and other synthetic antimicrobial amino acids, peptides, or proteins.

When the active agent is the antimicrobial agent, the antimicrobial agent is selected from the group consisting of chlorhexidine, octenidine, benzalkonium chloride, benzethonium chloride, polyhexamethylene biguanide, copper, zinc, silver, chlorine, an active chlorine compound, such as, but not limited to, sodium hypochlorite, fluoroquinolones, b-lactams, macrolides, aminoglycosides, tetracyclines, and combinations thereof.

In typical aspects, the antimicrobial agent comprises silver ions. In aspects, the silver ions are derived from a silver salt, for example, but not limited to, silver phosphate, silver sulfate, silver citrate silver lactate, silver acetate, silver benzoate, silver chloride, silver carbonate, silver iodide, silver iodate, silver nitrate, silver laurate, silver sulfadiazine, silver palmitate, and mixtures thereof.

When the matrices described herein comprise more than one layer, one or more active agents, may be present in and/or on any one or more of the multiple layers. In similar aspects, when the matrices described herein comprise one or more layers, one or more active agents may be present in and/or on all of the layers.

In further aspects, when the matrices described herein comprise more than one layer, the active agent described herein, the biomolecule described herein and/or the biocompatible polymer described herein are typically evenly or homogenously distributed through and/or on some or all of the layers. By "even" distribution, it is meant that the layers would have a uniform composition (i.e., no portion of the layer would have a substantially greater concentration or proportion of the biomolecule, the active agent and/or the biocompatible polymer, than another portion of the same layer and/or the adjacent layer). For example, if the matrix comprises two layers, a concentration of the biomolecule may be evenly distributed through a single layer, or evenly distributed through both layers. In this way, there are no "pockets" of space, or portions in the first layer that have an increased amount (e.g., concentration) of biomolecule, relative to another portion of the first layer, or even, for example, relative to the second layer.

In additional aspects, the biomolecule described herein and/or the biocompatible polymer described herein are unevenly or non-homogenously distributed through and/or on some or all of the layers. With respect to "uneven" distribution, it is meant that one or more of the layers would have at least one portion of the layer that has a varied (e.g., increased or decreased) concentration or proportion of the biomolecule, active agent and/or biocompatible polymer described herein, as compared to another portion of a different layer and/or the same layer. For example, if the matrix comprises two layers, the biocompatible polymer may have an increased proportion (e.g., concentration) in one portion of a first layer, as compared to another portion of the first layer, or even, for example, as compared to a portion or the whole of, a second layer. In this way, portions of the first layer, or the whole of the first layer may have a different biomolecule concentration, for example, from portions of or even the whole of the second layer. Varying the amount of the biomolecule within the layer(s) may be advantageous, for example, in producing a highly cross-linked matrix layer with increased absorbency, for contacting the wound.

It is understood that the "even" or "uneven" distribution of the biomolecule and/or the biocompatible polymer can be varied, by, for example, putting the same amount of the biomolecule and/or biocompatible polymer in each layer or by, for example, increasing or decreasing the amount of the biomolecule and/or biocompatible polymer that is in one layer as compared to another layer.

While two layers have been described, it is understood that a single layered foam matrix or a foam matrix having greater than two layers is within the scope of the present invention.

In addition, when the matrices described herein are layered, temporal and/or spatial separation of therapeutic effects may be achieved. For example, if the matrix has two layers of foam, and the active agent is placed in and/or on the layer of a matrix that is furthest from the skin, the active agent would then be temporally and spatially separated from the skin so as to delay the time of contact between the active agent and the skin. Conversely, if the active agent is placed in the skin contacting foam layer, the time of contact between the active agent and the skin would be decreased (especially if the active agent is placed on the surface of the layer and therefore in direct contact with the skin). It is also contemplated that when the matrices described herein comprise layers, the variety of therapeutic agents that may be included in the matrices described herein can be vastly increased. For example, different active agents, with differing concentrations, can be placed in and/or on different layers. So long as the active agent does not interfere with the foaming and/or stability of the matrices described herein, the active agent is considered within the scope of the invention described herein.

The matrices described herein are crosslinked. The matrices are crosslinked using a crosslinking agent. Typically, the crosslinking agents are rapid crosslinking agents.

In typical aspects, the crosslinking agent is selected from, but not limited to, 1-ethyl-3-(3-dimethylaminopropyl)carbodiimide (EDC), N-hydroxysuccinimide (NHS) and mixtures thereof.

In certain aspects, the matrices described herein are fabricated as a covering. The covering can be, but is not limited to, a wound barrier, a wound dressing, a hemostatic dressing, a vascular wrap, a sponge, a gauze, a bandage, a film, a sheet, a tube and combinations thereof.

The matrices described herein are crosslinked, absorbable sponges, which when produced by the methods described herein, lack the presence of undesirable surface-properties (e.g., the aforementioned "skin"), known to afflict gelatin sponge materials that are air-dried. Furthermore, the porous nature of the matrices described herein allow the matrices described herein to absorb many more times their weight in fluid, while at the same time remaining stable under physiological conditions.

Compositions

The matrices described above may be formed from a composition described herein. The composition comprises the biomolecule, as described above, wherein the biomolecule is crosslinkable and the composition is foamable in accordance with the description provided herein.

The composition comprises at least one biodegradable biomolecule. In typical aspects, the biomolecule is gelatin.

It will be understood that the biomolecule may be present in the matrices and/or the compositions described herein in any amount, typically from about 40% to about 80% by weight, such as from about 40%, 45%, 50%, 55%, 60%, 65%, 70%, or 75% to about 45%, 50%, 55%, 60%, 65%, 70%, 75% or 80% by weight.

In aspects, the composition further comprises the biocompatible polymer described herein. In typical aspects, the biocompatible polymer is alginate or carboxymethylcellulose.

It will be understood that the biocompatible polymer may be present in the matrices and/or the compositions described herein in any amount, typically from about 0.4% to about 25% by weight, such as from about 0.4%, 1%, 5%, 10%, 15%, or 20% to about 1%, 5%, 10%, 15%, 20% or 25% by weight.

In particular aspects, the compositions may comprise excipients, as would be understood to a skilled person. Non limiting examples of such excipients include, diluents, disintegrants; glidants; binders; lubricants; antioxidants; preservatives; coloring and flavoring agents; emulsifying and suspending agents; and pharmaceutical solvents. The use of excipients would be understood by the skilled person and exemplary lists such excipients can be found in, for example, Osol et al., Remington's Pharmaceutical Sciences (16$^{th}$ edition), 1980, 1225-1267 and 1367 and Liberman, et al., Pharmaceutical Dosage Forms: Tablets (volume 1), 1989, ISBN: 0-8247-8044-2, both of which are hereby incorporated by reference.

It will be understood that the excipient may be present in the composition in any amount, typically from 1% to 50% by weight, such as from about 1%, 5%, 10%, 15%, 20%, 25%, 30%, 35%, 40%, or 45%, to about 5%, 10%, 15%, 20%, 25%, 30%, 35%, 40%, 45% or 50% by weight.

When an additional therapeutic effect is desired, for example, in addition to providing a matrix that acts as a hemostat (e.g., wound dressing) to stop, limit, block, prevent or impede blood flow from a wound, the composition may further comprise an active agent that, for example, contributes the above described control of blood flow, or, for example, provides soothing relief to the pain associated with the wound. In typical aspects, if the composition further comprises the active agent as described herein, the active agent would be integral with the foam matrix (e.g., in and/or on the layer of the foam). If the active agent is desired to be on the surface of the foam produced by the methods described below, it would be understood that once the foam is made using the compositions described herein, the active agent can be applied to the dried foam, by either brushing a liquid concentrate of the active agent upon a surface of the foam or by spreading a powered form of the active agent upon a surface of the foam. Alternatively and/or additionally, the active agent can be spread on the tray or mold used to dry the foam, such that when the foam is spread on the tray or mold, a surface of the foam makes contact with the active agent. Accordingly, when the matrix is applied to a wound as a wound dressing, the active agent would be in immediate contact with a skin surface or wound, in order to provide additional therapeutic effects (e.g., in addition to the matrix providing a hemostat function).

It will be understood that the active agent may be present in the matrices and/or the compositions described herein in any amount, typically from about 0.1% to about 30% by weight, such as from about 0.1%, 1%, 5%, 10%, 15%, 20%, or 25% to about 1%, 5%, 10%, 15%, 20%, 25% or 30% by weight.

In alternative or additional aspects, the compositions described herein further comprise the crosslinking agent described herein. The matrices and/or compositions described herein are substantially free of crosslinking agent which advantageously contributes to a lower toxicity profile of the matrices and/or compositions.

It will be understood that the crosslinking agent may be present in the matrices and/or the compositions described herein in any amount, typically from about 0.5% to about 5% by weight, such as from about 0.5%, 1%, 1.5%, 2%, 2.5%, 3%, 3.5%, 4%, or 4.5% to about 1%, 1.5%, 2%, 2.5%, 3%, 3.5%, 4%, or 4.5% or 5% by weight.

The compositions described herein are useful for making the dried crosslinked, foamed matrices described herein.

Methods of Making the Matrices and Uses Thereof

Described herein are methods of forming the matrices described herein. The method comprises foaming the compositions comprising the biomolecule described above, crosslinking the compositions described above and drying the composition described above.

The method utilizes foaming and crosslinking steps. Typically, the crosslinking is carried out while foaming. In aspects, the crosslinking is carried out after foaming.

In aspects, the biomolecule is selected from gelatin, collagen, elastin, and combinations thereof. Typically, the biomolecule is gelatin. To produce a solution of the biomolecule, in aspects, water is mixed to create a small vortex to which the biomolecule is added. Typically, the biomolecule is added slowly to allow for even dispersal in the water. In aspects, this solution is heated with continuous agitation until the biomolecule is completely dissolved. In aspects, the heating is at a temperature of about 50° C. That is, the temperature is 45° C., 46° C., 47° C., 48° C., 49° C., 50° C., 51° C., 52° C., 53° C., 54° C. or 55° C.

The solution may be a combination of the biomolecule and the biocompatible polymer. In this way, in aspects, the composition further comprises the biocompatible polymer as described herein. In typical aspects, the biocompatible polymer is alginate or carboxymethylcellulose. When the composition comprises both the biomolecule and the biocompatible polymer, a solution of the biocompatible polymer (e.g., alginate) is likewise prepared by, for example, mixing water to create a small vortex and adding the biocompatible polymer or salt thereof (e.g., sodium alginate) to the water. In aspects, the biocompatible polymer or salt thereof is added slowly to minimize clumping.

Typically, this solution is heated with continuous agitation until the biocompatible polymer is completely dissolved. In aspects, the heating is at a temperature of about 50° C. That is, the temperature is 45° C., 46° C., 47° C., 48° C., 49° C., 50° C., 51° C., 52° C., 53° C., 54° C. or 55° C. In this way, a solution of biomolecule or a biocompatible solution is produced.

When an antimicrobial foam is desired, in aspects, an active agent, such as silver (in the form of a salt, e.g., silver lactate) is added to water and stirred to form a homogenous mixture. The silver lactate solution is then added to the biomolecule solution and this solution is heated to about 60° C. with continuous agitation to ensure that the biomolecule is completed dissolved. At this point, another salt (such as sodium chloride) is added to initiate the formation of silver chloride in solution.

Heating the solutions as described herein ensures that homogenous solutions of the biomolecule or the biocompatible polymer are produced.

When a combination of biomolecule and biocompatible polymer solution is desired, after heating each solution, the biocompatible polymer solution (e.g., alginate) is added to the biomolecule solution (e.g., gelatin). Typically, this addition is done slowly to ensure that thorough mixing takes place. For example, a homogenous mixture (solution) of biomolecule and biocompatible polymer is produced.

When only a biomolecule solution is desired, after heating, the crosslinking agent described herein, is added to the solution. Typically, the crosslinking agents are rapidly crosslinking agents. Typically, the crosslinking agent is EDC and/or NHS. In aspects, a combination of crosslinking agents may be prepared and added to the biomolecule or biomolecule-biocompatible polymer solutions described herein. In aspects, the solution is agitated until there is complete dissolution of the crosslinking agent in the biomolecule solution. For example, a homogenous mixture of crosslinking agent and biomolecule is produced.

When a biomolecule and biocompatible polymer solution (e.g., alginate or carboxymethylcellulose) is produced by adding the biocompatible polymer solution to the biomolecule solution, in aspects, a temperature of the solution is adjusted to about 30° C. to about 40° C.

In aspects, additional agents, such as, but not limited to, chelators (e.g., ethylenediaminetetraacetic acid (EDTA)) or lipids (e.g., glycerol) are added to the biomolecule biocompatible polymer solutions. One of skill in the art would understand that different additional agents may be added to the solutions to, for example, assist in dissolution of the components of the solution.

In typical aspects, another crosslinking agent, (e.g., NHS or EDC depending on which was not used as described above) is prepared prior to addition to the above described solutions (e.g., the gelatin solution or the gelatin-alginate solutions).

Typically, the temperature of the biomolecule, biocompatible polymer solution is cooled to about 25° C. to about 28° C. to begin the foaming process. In aspects, the solution is cooled to 23° C., 24° C., 25° C., 26° C., 27° C., 28° C., 29° C., or 30° C. Reducing the temperature of the mixture is advantageous to ensure the chemical activity of the crosslinking agents (e.g., EDC and NHS) as well as to provide the right viscosity for foaming as described herein. Typically, the cooling is done with continuous stirring to create a foaming solution. After cooling, the foaming solution is transferred to a bowl in a stand mixer for foaming. In aspects, the solution is mixed or foamed at maximal speed for about 4 minutes. In aspects, the mixing time is 3 minutes, 4 minutes or 5 minutes. In typical aspects, the speed of mixing is 495 RPM. Typically, while mixing is occurring, the other crosslinking agent is added to the foaming solution. For example, the adding of the crosslinking agent is done in combination with the foaming. In aspects, the addition of the crosslinking agent is done slowly within a period of time. In aspects, the period of time is about 30 seconds. In aspects, the period of time is 20 seconds, 25 seconds, 30 seconds, or 35 seconds (or any value therebetween).

The addition of the crosslinking agent can be carried out in any manner. For example, the crosslinking agent could be prepared as a separate solution and added fully during the foaming process. For example, the crosslinking agent could be prepared as a separate solution and added (in full) to the above described solutions of biomolecules and biocompatible polymers, after the foaming process. Typically, the addition of the other crosslinking agent is carried out in a dropwise manner (e.g., by using a serological pipette) such that all of the solution is dispensed within a short period of time. Dropwise addition of the other crosslinking agent allows for even distribution of the other crosslinking agent within the solution of the biomolecule and biocompatible polymer during the foaming process. For example, since there is less volume per unit time of the other crosslinking agent to mix with the total volume of the solution to which it is being added, dissolution time of the other crosslinking agent is quicker. In aspects, the short period of time is about 30 seconds. In aspects, the period of time is 20 seconds, 25 seconds, 30 seconds, or 35 seconds (or any value therebetween).

Typically, once all of the other crosslinking agent (e.g., NHS or EDC) has been mixed into the foaming solution, the foaming solution is continually mixed for another period of time. Continual mixing aids in the foaming process and increases the volume (expansion) of the foam as described below. Typically, this period of time is about 10 seconds. In aspects, the period of time is 5 seconds, 6 seconds, 7 seconds, 8 seconds, 9 seconds, 10 seconds, 11 seconds or 12 seconds.

In aspects, the mixing is continued until the foam increases in volume. In other words, the mixing is continued until the foam forms with a total volume expansion of about 3 times to about 10 times the initial solution volume. In aspects, the increased volume is about 2 L. In aspects, the increased volume is 1 L, 1.5 L, 2 L or 2.5 L (or any value therebetween). In aspects, the increase in the volume of the foam takes place in about 5 minutes.

After the foam is produced, the foam is removed from the bowl and dispensed and spread into a tray or a mold. In aspects, the tray or mold has a pre-applied layer of active agent(s) as described herein. For example, the active agent described herein may be spread onto a surface of the tray or mold so that when the foam is placed on that surface, and therefore in contact with the active agent, the active agent may be layered onto a surface of the matrix contacting the tray or mold. It is contemplated that this layering process may be even (e.g., uniform) or uneven (e.g., non-uniform), depending on, for example, the spread of the active agent on the surface of the tray or mold, the adhesive properties of the surface of the matrix that contacts the active agent, and/or the length of time that the matrix remains in contact with the surface of the tray or mold.

In aspects, the tray or mold is lined with a hydrophobic film, so as to, for example, provide a non-stick surface on the tray or mold, for application of the foam described herein.

The time for removing the foam from the bowl and spreading the foam in the tray or mold can be varied, for example, it could be removed and spread within 10 seconds of formation of the foam, or it can be removed and spread within 60 seconds of formation of the foam. In aspects, the foam is removed from the bowl in less than 15 seconds. In aspects, the foam is spread in less than or equal to 60 seconds. Once the foam is spread on the tray or mold, it is dried. In typical aspects, the foam is air-dried, such that the moisture from the foam is removed. Typically, the foam is then dried for a period of time. In aspects, the period of time is up to 48 hours. In aspects, the period of time is 1 hour, 3 hours, 5 hours, 8 hours, 12 hours, 16 hours, 20 hours, 30 hours, 40 hours, or 48 hours (or any period of time therebetween).

As noted above, the matrices described herein are not lyophilized and are, instead, air-dried. Typically, the air-drying is carried out in ambient pressure and temperature (e.g., 25 C (298.15 K) and pressure of 101.325 kPa), however, other temperatures are considered within the scope of the invention as described below. In typical aspects, the drying is carried out by using ventilators to ensure efficient air circulation around the foam. By providing efficient air circulation around the foam, the drying process may ensure that there are no "wet spots" on the foam. Typically, the foam produced by the drying methods described herein, is not a moist foam. In aspects, the foam has substantially no moisture so that the foam is substantially dry (e.g., at least about 90% dry).

Once the foam is dried, the dried sponge (e.g., a gelatin sponge or a gelatin-alginate sponge) is removed from the tray and cut to desired size. The size of the sponge is dependent on the needs of the user. It is understood that the size and/or the shape of the sponge can be varied by, for example, cutting the sponge to the size or shape, changing the shape or size of the tray or mold, or by varying the amount of foam that is applied to the tray or mold.

In typical aspects, the drying and cutting is carried out at a temperature of less than or equal to about 40° C. and a relative humidity of about 35%. In aspects, the temperature is about 20° C., about 25° C., about 30° C., about 35° C., or about 40° C. (or any value therebetween). In aspects, the relative humidity is about 33%, about 34%, about 35%, about 36% or about 37%. Methods of cutting the sponges produced by the methods described herein would be understood by those of skill in the art.

In addition, the compositions used for making the matrices described herein according to the method described herein may also comprise the active agent described herein. Typically, the active agent does not substantially affect the foaming described herein. In aspects, instead of the composition comprising the active agent described herein, the active agent described herein may be layered onto the foam (e.g., the active agents described herein are layered onto a top layer of the foam) produced by the method described herein. As also described herein, the active agent may be applied to the surface of the tray or mold and when the foam is applied (e.g., spread) on the tray or mold, the active agent can adhere to the surface of the foam and/or the pores. In aspects, the active agent is in a powdered or concentrated liquid form. For example, a pre-applied layer of powdered active agent can be applied to the tray or mold such that contact between the foam and the tray or mold results in the powdered active agent on the surface of the foam. Alternatively, the active agent in liquid form could be applied to the dried foam, subsequent to, or after removal of the dried foam from the tray or mold. It is understood that the addition of the active agent can be varied, as described above, so long as the active agent does not substantially affect the foaming described herein and/or the stability of the foam so produced.

The foam produced by the methods described herein may consist of a single layer (e.g., the methods described herein are carried out and the dried foam produced may be used as a wound dressing), or the foam may comprise more than one layer. If the foam comprises multiple layers (e.g., at least two layers), the methods described herein would be repeated and each layer can be joined together to form an integral composite. In aspects, the foam produced by the methods described herein comprises at least two layers. In aspects, the active agent can be layered onto or into at least one of the at least two layers. For example, layering active agent onto a layer (i.e., single or multiple), can be done by either directly applying the active agent onto the surface of the foam, or by, for example, applying the active agent onto the tray or mold and allowing contact with the foam during the spreading. Alternatively or additionally, the active agent can be put into the compositions described herein and therefore the active agent is a component of an internal portion of the foam layer. These examples advantageously allow for temporal and/or spatial separation of potential therapeutic effects and may broaden the variety of active agents that can be employed in the invention described herein. For example, if one active agent is placed on the surface of the foam that contacts the skin, and another (e.g., the same or different active agent) is placed within the foam layer, the active agent closest to the skin would have an immediate or fast therapeutic effect, whereas the active agent in the foam layer would be temporally controlled (e.g., the active agent percolates through the porous foam), to provide a benefit to the user at a later time point.

The method described above may be fully manual, fully automated, or partially automated.

An advantage to the methods described herein for making the matrices described herein is that the methods described herein allow for near instantaneous crosslinking of foamed (e.g., gelatin) solutions followed by an air-drying process performed, typically, at ambient pressure and temperature, without the formation of a hardened and/or compacted "skin" or film-like substance on the surface of the sponge that contacts the drying container. Accordingly, further processing of the matrices described herein to remove the presence of undesirable surface layers (e.g., the aforementioned "skin") is avoided. Furthermore, since the methods described herein do not require lyophilization, the requirement of large and expensive equipment to obtain a porous matrix through freeze-drying is also avoided. In this way, the procedure to produce the foam matrix of the present invention is greatly simplified and produces a product that lacks physical abnormalities, such as the hardened or compacted skin described herein.

Furthermore, methods and uses of the compositions and matrices are described herein. As described herein, the matrices and compositions for making the matrices described herein, can be used to reduce microorganism growth on a surface (see, also Example 3 and 5). In this regard, the above described solutions of biomolecule and biocompatible polymer, further comprises silver, for example, as the active agent. As described herein, the active agent) can be included on the surface of the foam layer or it may be an integral part of the foam layer. In aspects, the microorganism is selected from, but not limited to, *Candida albicans, Escherichia coli*, and antibiotic-resistant *Enterococcus*.

To use the sponge made by the methods described herein for antimicrobial activity, it is applied (e.g., laid onto, adhered to) a surface. The surface is suspected of having, or has been confirmed to have one or more microorganisms. Application, such as laying or adhering, of the sponge to the surface is a method of controlling the growth and/or spread of the one or more microorganisms. In aspects, the surface is a skin surface. In aspects, the surface is a surface of an inanimate object, such as, but not limited to, a table, a chair, or a countertop. In aspects, the surface is a surface of a medical device. In this way, the matrices described herein can be used to clean (e.g., sterilize) medical devices and other inanimate objects.

The medical device is typically a device for use internally or for external use on wounds, for example. Thus, in particular aspects, the medical device is selected from the group consisting of dressings, scaffolds, fracture fixation devices, catheters, stents, implants, tubings, rods, prostheses, endoscopes, cardiac valves, pacemakers, dental implants, and surgical, medical or dental instruments.

In aspects, the matrices described herein are used as a wound dressing, a bandage, or a sponge. Typically, the matrices are effective hemostats useful for treating a wound or an injury. Typically, the wound or injury is with respect to a skin surface. Also described herein are methods of treating the wound or injury, the method comprising applying the matrices described herein, to the wound or injury site. The applying can be for example, laying the matrix on the skin or wound (e.g., covering the skin or wound with the matrix), inserting the matrix into the wound (e.g., to fill the wound with the matrix), or adhering the matrix to the skin or wound (e.g., the adhering may be through a medical-grade adhesive applied to the surface of the wound, followed by application of the matrix to the adhesive, or application of the medical-grade adhesive to the matrix, followed by application of the matrix to the wound). In this way, uses of the matrices described herein are contemplated to treat a wound or injury site. For example, application of the matrix as described herein may treat the wound or injury site by stopping, slowing down, or preventing further bleeding. For example, application of the matrix to the wound or injury site may prevent other objects from entering the wound or injury site. In additional examples, application of the matrix may allow for delivery of the active agent, which contributes to wound repair and/or provides soothing pain relief. In typical aspects, the wound or injury site is with respect to a skin surface.

Accordingly, the matrices described herein have a variety of applications, including, but not limited to, wound dressings and barriers, surgical dressings, hemostatic dressings, and in therapeutic drug and/or chemical agent delivery. For example, it is contemplated that application of the active agent described herein to the surface of the matrices described herein, followed by application of the matrix to, for example the skin, would not only be useful in treating the wound but would also allow delivery of the active agent to the wound or skin as described above, thereby providing additional and/or alternative therapeutic effect(s).

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Example 1—Gelatin Sponge

A gelatin sponge, within the scope of the invention described herein was formed as follows:

Purified water (500 mL) was added into a 1 L flask or container. The water was mixed to create a small vortex and 36 g of porcine gelatin was added to the water. Gelatin was added slowly for even dispersal in the liquid. The flask or container was covered and heated to 50° C. with continuous agitation until the gelatin was completely dissolved. Then, 0.52 g of NHS was added and the solution was agitated until completely dissolved.

Purified water (10 mL) was added to a 50 mL Falcon tube or container. An EDC solution was prepared immediately prior to use by adding 2.8 g of EDC to the water and agitating the solution until completely dissolved.

The Gelatin/NHS mixture was cooled to 25-28° C. (with continuous stirring) to create a foaming solution. The foaming solution was transferred into a bowl of a stand mixer. Then, the solution was mixed/foamed at maximum speed for 1 minute. While the mixing was continued, a 20 mL serological pipette was used to add the EDC solution into the bowl in a dropwise manner, such that all of the solution was dispensed within 30 seconds. The added EDC droplets were mixed into the solution immediately. After all of the EDC solution was dispensed, mixing was continued for another 10 seconds.

Then, the foam was immediately dispensed and spread into a tray.

Next, the foam was dried for up to 48 hours. Ventilators were used to ensure efficient air circulation around the foam. Once dried, the gelatin sponge was removed from the tray and directly cut to desired size for final packaging and processing.

Example 2—Gelatin-Alginate Sponge

A gelatin-alginate sponge, within the scope of the invention described herein was formed as follows:
Gelatin Solution
Purified water (500 mL) was added into a 1 L flask or container. The water was mixed to create a small vortex and then 36 g of fish gelatin was added. The gelatin was added slowly for even dispersal in the liquid. The flask or container was covered and heated to 50° C. with continuous agitation until the gelatin was completely dissolved.
Alginate Solution
Purified water (490 mL) was added to a 1 L flask or container. The water was mixed and 0.25 g of sodium hydroxide was added and mixed for 3 to 5 minutes until visually dissolved. The mixing speed was increased to create a small vortex and the 40 g of sodium alginate was added slowly to minimize clumping. The flask or container was covered and heated to 50° C. with continuous agitation until the alginate was completely dissolved.

Gelatin/Alginate/Glycerol/NHS Solution

The alginate solution was slowly added into the gelatin solution ensuring that thorough mixing occurred. The temperature of the gelatin/alginate solution was reduced to 30° C. Then, 2.0 g of glycerol (1.59±0.03 mL) was added and agitated until thoroughly mixed. Then, 0.52 g of NHS was added and agitated until completely dissolved.

EDC Solution

Purified water (10 mL) was added to a 50 mL Falcon tube or container. The EDC solution was prepared immediately prior to use by adding 2.8 g of EDC to the water and agitating the solution until completely dissolved.

Foaming

The Gelatin/Alginate/Glycerol/NHS mixture was cooled to 25-28° C. (with continuous stirring) to create a foaming solution. The foaming solution was transferred into a bowl of a stand mixer. Then, the foaming solution was mixed/foamed at maximum speed for 4 minutes. While the mixing was continued, a 20 mL serological pipette was used to add the EDC Solution into the bowl in a dropwise manner, such that all of the solution was dispensed within 30 seconds. The added EDC droplets were mixed into the solution immediately. After dispensing all of the EDC solution, mixing was continued for another 10 seconds.

Then, the foam was immediately dispensed and spread into a tray.

Drying and Sizing

The foam was dried for up to 48 hours. Ventilators were used to ensure efficient air circulation around the foam. The dried gelatin-alginate sponges were removed from the tray and directly cut to desired size for final packaging and processing.

Example 3—Antimicrobial Gelatin-Carboxymethyl Cellulose (CMC) Sponge

An antimicrobial gelatin-CMC sponge, within the scope of the invention described herein was formed as follows:

Gelatin Solution

Purified water (245 mL) was added into a 1 L flask or container. The water was mixed and 1.90 g of silver lactate was added. The solution was mixed until silver lactate dissolved (approximately 5-10 minutes). A small vortex was created by increasing the mixing speed and 12.0 g of gelatin was added to the solution. The gelatin was added slowly for even dispersal in the liquid. The flask or container was covered and heated to 60° C. with continuous agitation until the gelatin was completely dissolved. Sodium chloride (0.56 g) was slowly added to initiate formation of silver chloride.

CMC Solution

Purified water (250 mL) was added into a 2 L flask or container. Next, 0.10 g sodium hydroxide was added and mixed for 3 to 5 minutes until visually dissolved. The mixing speed was increased to create a small vortex and 2.85 g of CMC was added to minimize clumping. The flask or container was covered and heated to 60° C. with continuous agitation until the CMC was completely dissolved.

Gelatin/CMC Solution

The gelatin solution was slowly added into the CMC solution ensuring that thorough mixing occurred (agitating for about 1 hour). The temperature of the gelatin/CMC solution was reduced to 25° C.

EDTA Solution

EDTA (calcium disodium salt) (2 g) was placed in a 50 mL Falcon tube and 5 mL of water was added into the Falcon tube. The solution was mixed with shaking until EDTA was dissolved. This solution was added into the gelatin/CMC solution and mixed for at least 5 minutes.

EDC/NHS Solution (Prepare Immediately Before Use)

EDC (0.65 g) and NHS (0.10 g) were transferred into a 50 ml Falcon tube. Next, 2.5 mL of water was added into the Falcon tube with EDC/NHS. The solution was mixed with shaking until EDC/NHS was dissolved (a mixing time of 15 minutes was not exceeded before use).

Foaming

The mixture (0.5 L) was transferred to a mixing bowl. Next, the mixture was mixed (blended) at maximal speed until the volume of the foam increased to about 2 L (approximately 5 minutes). Then, EDC/NHS crosslinkers were slowly added to the foam within 30 seconds. Then, the foaming was continued for an additional 10 seconds.

Next, the foam was immediately dispensed and spread into a tray.

Drying and Sizing

The foam was dried for up to 48 hours. Ventilators were used to ensure efficient air circulation around the foam. Then, the dried gelatin-CMC sponge was removed from the tray and directly cut to desired size for final packaging and processing.

Example 4—Antimicrobial Activity

The antimicrobial activity of samples prepared according to Example 3 above were tested in a growth inhibition assay using the microorganisms *Escherichia coli* (ATCC 8739), vancomycin-resistant *enterococcus* (ATCC 51575) and *Candida albicans* (ATCC 10231).

TABLE 1

Zone of inhibition assay of antimicrobial gelatin-CMC sponges.

| Species | Zone of Inhibition (mm) | | |
|---|---|---|---|
| | Day 1 | Day 2 | Day 3 |
| E. coli | 9 | 8 | 7 |
| VRE | 4 | 3 | 2 |
| C. albicans | 3 | 2 | 1 |

Example 5—Comparative Freeze-Dried Sponge

A gelatin sponge that was freeze-dried was produced as follows:

Silver lactate (0.965 g) was added to 600 mL of water at 50° C. and the solution was mixed until complete dissolution of the silver salt was achieved. Subsequently, 0.289 g of silver chloride was added to the silver solution to form a suspension of silver chloride. Gelatin (275 Bloom; 5.778 g) was then added to the silver chloride suspension and the mixture was stirred until the gelatin was dissolved. In a separate container, 1.133 g of CMC was added to 400 mL of alkaline water (pH 9.0) at 50° C. and the mixture was stirred until all of the CMC was dissolved. The gelatin/silver chloride suspension and CMC solution were mixed and 1.0 g of sodium EDTA was added with stirring until complete dissolution of the EDTA. In a final step, 0.909 g of EDC and 0.140 g of NHS were added to the biopolymer mixture and stirred until dissolved. After an additional 15 minutes of mixing, aliquots of the biopolymer mixture were poured into plastic trays and freeze-dried for 24 hours resulting in gelatin/CMC sponges containing silver.

Example 6—Silver Elution

Antimicrobial sponges (gelatin/CMC with silver) prepared according to Example 3 above were compared to gelatin/CMC with silver sponges prepared according to Example 5 above with respect to their silver elution profiles.

In brief, samples of each type of antimicrobial sponge were incubated in saline maintained at 37° C. with stirring. At selected intervals, aliquots of the eluate were removed for analysis of silver content via atomic absorption spectroscopy. The results of the silver elution assay are shown in Table 2.

TABLE 2

Comparison of silver elution profile of antimicrobial sponges according to Example 3 and Example 5

| Antimicrobial Sponge | Day 1, [Ag], µg/cm$^2$ | Day 3, [Ag], µg/cm$^2$ | Day 7, [Ag], µg/cm$^2$ |
|---|---|---|---|
| Example 3 | 14.4 ± 1.1 | 18.5 ± 1.7 | 23.7 ± 0.4 |
| Example 5 | 13.0 ± 1.4 | 19.0 ± 1.5 | 25.0 ± 2.3 |

As illustrated above, silver release from the two types of antimicrobial sponges was essentially identical demonstrating the similar properties of the final products with respect to silver elution despite the different methods (i.e., air-drying in accordance with present invention versus freeze-drying) used to prepare the sponges.

Example 7—Physical Properties

Sponge samples prepared according to Examples 1, 2, and 3 as well as comparative Example 5 were characterized with respect to their crosslinking extent, heat stability and water absorbency. The water absorbency of the gelatin matrices was measured according to a procedure involving the differential weight measurement of samples pre- and post-incubation in 37° C. water for 1 h. The heat stability of samples was also evaluated at this point. The crosslinking extent was determined in a similar manner except the samples were incubated in 37° C. water for 16 h and then dried before measurement of the post-incubation sample weight.

The crosslinking extent, heat stability, and water absorbency (expressed as grams of water absorbed per gram of material) of the test samples are shown in Table 3.

TABLE 3

Physical properties of selected crosslinked gelatin sponges.

| Sample | Crosslinking Extent (%) | Heat Stability | Water Absorbency (g/g) |
|---|---|---|---|
| Gelatin Sponge | 72 | Pass | 29 |
| Gelatin-Alginate Sponge | 74 | Pass | 26 |
| Antimicrobial Gelatin-CMC Sponge | 71 | Pass | 36 |
| Comparative Antimicrobial Gelatin-CMC Sponge | 54 | Pass | 18 |

The above disclosure generally describes the present invention. Although specific terms have been employed herein, such terms are intended in a descriptive sense and not for purposes of limitation.

All publications, patents and patent applications cited above are herein incorporated by reference in their entirety to the same extent as if each individual publication, patent or patent application was specifically and individually indicated to be incorporated by reference in its entirety.

Although preferred embodiments of the invention have been described herein in detail, it will be understood by those skilled in the art that variations may be made thereto without departing from the spirit of the invention or the scope of the appended claims.

What is claimed is:

1. A matrix comprising (i) a biomolecule selected from the group consisting of gelatin, collagen, elastin, and combinations thereof; (ii) a biocompatible polymer selected from the group consisting of polyethylene glycol, poly-L-lysine, alginate, chitosan, hyaluronic acid, chondroitin sulfate, pectin, cellulose, carboxymethylcellulose and mixtures thereof; and (iii) an active agent; and wherein the biomolecule and biocompatible polymer are evenly distributed throughout the matrix; wherein the matrix is a dried, cross-linked foam; wherein the biomolecule is present at about 40% to about 80% (w/w) by the weight of said matrix; and wherein said matrix is non-lyophilized and has an absorption capacity of about 20 times to about 50 times a dry weight of the matrix.

2. The matrix of claim 1, wherein the biomolecule is gelatin.

3. The matrix of claim 1, wherein the biocompatible polymer is carboxymethylcellulose and is present in about 0.4% to about 25% (w/w) by the weight of the matrix.

4. The matrix of claim 1 having a pore size ranging from about 100 µm to about 750 µm, and/or a thickness of at least 1 mm.

5. The matrix of claim 1, wherein the active agent is selected from the group consisting of an antimicrobial agent, an analgesic agent, an anti-adhesion compound, an anti-tumor drug, an anti-proliferative drug, a chelator and combinations thereof.

6. The matrix of claim 5, wherein the antimicrobial agent is selected from the group consisting of chlorhexidine, octenidine, benzalkonium chloride, benzethonium chloride, polyhexamethylene biguanide, copper, zinc, silver, chlorine, an active chlorine compound, fluoroquinolones, b-lactams, macrolides, aminoglycosides, tetracyclines, and combinations thereof.

7. The matrix of claim 5, wherein the antimicrobial agent comprises silver ions derived from a silver salt selected from the group consisting of silver phosphate, silver sulfate, silver citrate, silver lactate, silver acetate, silver benzoate, silver chloride, silver carbonate, silver iodide, silver iodate, silver nitrate, silver laurate, silver sulfadiazine, silver palmitate, and mixtures thereof.

8. The matrix of claim 1, wherein the matrix is cross-linked using a crosslinking agent selected from the group consisting of 1-ethyl-3-(3-dimethylaminopropyl)carbodiimide, N-hydroxysuccinimide and mixtures thereof in an amount of about 0.5% to about 5% (w/w).

9. The matrix of claim 1, wherein the matrix is selected from the group consisting of a wound barrier, a wound dressing, a hemostatic dressing, a vascular wrap, a sponge, a gauze, a bandage, a film, a sheet, a tube and combinations thereof.

10. A method of treating a wound comprising applying the matrix of claim 1 to the wound.

11. A method for making the matrix of claim 1, the method comprising:
foaming a composition comprising a biomolecule;
crosslinking the composition; and
drying the composition.

12. The method of claim 11, wherein the biomolecule is selected from the group consisting of gelatin, elastin, collagen, and combinations thereof.

13. The method of claim 11, wherein the crosslinking is carried out during or after the foaming step by using a crosslinking agent selected from the group consisting of 1-ethyl-3-(3-dimethylaminopropyl)carbodiimide, N-hydroxysuccinimide, and mixtures thereof.

14. The method of claim 11, wherein the composition further comprises at least one biocompatible polymer selected from the group consisting of polyethylene glycol, poly-L-lysine, alginate, chitosan, hyaluronic acid, chondroitin sulfate, pectin, cellulose, carboxymethylcellulose and mixtures thereof.

15. The method of claim 11, wherein the composition further comprises an active agent.

16. The method of claim 15, wherein the drying step comprises air-drying and excludes lyophilizing.

17. The method of claim 15, wherein the air-drying is carried out at ambient pressure and temperature.

18. The matrix of claim 1, wherein cross-linking is carried out while foaming the matrix.

\* \* \* \* \*